United States Patent [19]
Ryono et al.

[11] Patent Number: 5,635,504
[45] Date of Patent: Jun. 3, 1997

[54] DIAZEPINE CONTAINING DUAL ACTION INHIBITORS

[75] Inventors: Denis E. Ryono, Princeton; Chong-Oing Sun, East Windsor, both of N.J.

[73] Assignee: Bristol-Myers Squibb Co., Princeton, N.J.

[21] Appl. No.: 609,184

[22] Filed: Mar. 1, 1996

Related U.S. Application Data

[63] Continuation-in-part of Ser. No. 474,041, Jun. 7, 1995, abandoned.

[51] Int. Cl.$^6$ .................. A61K 31/55; C07D 243/02
[52] U.S. Cl. .................. 514/218; 540/492; 540/500; 544/232; 544/238; 544/239; 514/221; 514/227; 514/248
[58] Field of Search ............... 540/492, 500; 544/232, 238, 239; 514/218, 221, 247, 248

[56] References Cited

U.S. PATENT DOCUMENTS

| 3,856,798 | 12/1974 | Meyer et al. | 260/294.8 |
| 4,105,776 | 8/1978 | Ondetti et al. | 424/274 |
| 4,186,200 | 1/1980 | Kubo et al. | 424/256 |

(List continued on next page.)

FOREIGN PATENT DOCUMENTS

| 249223 | 12/1987 | European Pat. Off. . |
| 249224 | 12/1987 | European Pat. Off. . |
| 481522 | 4/1992 | European Pat. Off. . |
| 524553 | 1/1993 | European Pat. Off. . |
| 534363 | 3/1993 | European Pat. Off. . |
| 534396 | 3/1993 | European Pat. Off. . |
| 534492 | 3/1993 | European Pat. Off. . |
| 595610 | 5/1994 | European Pat. Off. . |
| 599444 | 6/1994 | European Pat. Off. . |
| 629627 | 12/1994 | European Pat. Off. . |
| 2207351 | 2/1989 | United Kingdom . |
| WO93/16103 | 8/1993 | WIPO . |
| WO94/10193 | 5/1994 | WIPO . |
| WO94/26719 | 11/1994 | WIPO . |
| WO94/28901 | 12/1994 | WIPO . |

OTHER PUBLICATIONS

Adams et al., Synthetic Communications, vol. 18, 2225–2231 (1988).
Attwood et al., FEBS Letters, vol. 165, pp. 201–206 (1984).
Attwood et al., J. Chem. Soc. Perkin Trans I (1986) pp. 1011–1019.
Bolos et al., J. Org. Chem., 57, 3535–3539 (1992).
Bolos et al., Tetrahedron, vol. 48, pp. 9567–9576 (1992).
Boyer, T. D. "Cirrhosis of the Liver and Its Major Sequelae" in: Wyngaarden, J. B. et al., Cecil Textbook of Medicine, vol. 1 (Saunders Co., 1992) pp. 786–789.
Chackalamannil et al., Bioorganic & Medicinal Chemistry Letters, vol. 2, pp. 1003–1006 (1992).
Das et al., Bioorganic & Medicinal Chemistry Letters, vol. 4, pp. 2193–2198 (1994).
Delaney et al., Bioorganic & Medicinal Chemistry Letters, vol. 4, pp. 1783–1788 (1994).
Dussaule et al., Jour. of Clinical Endocrinology and Metabolism, vol. 72, pp. 653–659 (1991).
Fernandez–Cruz, The Lancet, Dec. 21/28, pp. 1439–1440 (1985).
Flynn et al., J. Med. Chem., 36, pp. 2420–2423 (1993).
Flynn, Tetrahedron Letters, vol. 31, pp. 815–818 (1990).
Fobian et al., 206th Meeting of the Amer. Chem. Society, Aug. 1993 Abstr. ORG 297.
Fyhrquist et al., The Lancet, Dec. 21/28, p. 1439 (1985).
Hanau et al., 206th Meeting of the Amer. Chem. Society, Aug. 1993 Abstr. ORG 298.
Itoh et al., Chem. Pharm. Bull., vol. 34, pp. 1128–1147 and 2078–2089 (1986).
Laffi et al., Gastroenterology, vol. 96, pp. 167–177 (1989).
Moeller et al., Tetrahedron Letters, vol. 33, pp. 6041–6044 (1992).
Naming and Indexing of Chemical Substances for Chemical Abstracts, 1987 Index Guide, Section 203.
Natoff et al., Drugs Of the Future, vol. 12, pp. 475–483 (1987).
Parsons et al., Biochem and Biophysical Research Comm. 117, pp. 108–113 (1983).
Robl et al., Bioorganic & Medicinal Chemistry Letters, vol. 4, pp. 1789–1800 and 2055–2060 (1994).

(List continued on next page.)

*Primary Examiner*—Robert T. Bond
*Attorney, Agent, or Firm*—Stephen B. Davis

[57] ABSTRACT

Compounds of the formula wherein:

A is are dual inhibitors of NEP and ACE. Compounds wherein A is are selective ACE inhibitors.

17 Claims, No Drawings

U.S. PATENT DOCUMENTS

| | | | |
|---|---|---|---|
| 4,192,945 | 3/1980 | Ondetti | 546/245 |
| 4,225,495 | 9/1980 | Ondetti | 260/244.4 |
| 4,337,201 | 6/1982 | Petrillo, Jr. | 548/413 |
| 4,339,600 | 7/1982 | Ondetti et al. | 562/426 |
| 4,374,829 | 2/1983 | Harris et al. | 424/177 |
| 4,409,146 | 10/1983 | Thorsett et al. | 260/239.3 |
| 4,410,520 | 10/1983 | Watthey | 424/244 |
| 4,415,496 | 11/1983 | Harris et al. | 260/239.3 |
| 4,432,971 | 2/1984 | Karanewsky et al. | 424/177 |
| 4,432,972 | 2/1984 | Karanewsky et al. | 424/177 |
| 4,460,579 | 7/1984 | Karanewsky | 424/200 |
| 4,465,679 | 8/1984 | Huang et al. | 424/244 |
| 4,470,988 | 9/1984 | Watthey | 424/263 |
| 4,473,575 | 9/1984 | Watthey | 424/263 |
| 4,477,464 | 10/1984 | Slade et al. | 424/275 |
| 4,512,924 | 4/1985 | Attwood et al. | 260/243.3 |
| 4,537,885 | 8/1985 | Watthey | 514/183 |
| 4,539,150 | 9/1985 | Katakami et al. | 260/239.3 |
| 4,548,932 | 10/1985 | Sugihara et al. | 514/211 |
| 4,575,503 | 3/1986 | Watthey | 514/213 |
| 4,584,294 | 4/1986 | Ruyle | 514/214 |
| 4,587,050 | 5/1986 | Harris et al. | 260/239.3 |
| 4,587,238 | 5/1986 | Harris et al. | 514/183 |
| 4,594,341 | 6/1986 | Cheung et al. | 514/211 |
| 4,617,301 | 10/1986 | Patchett et al. | 514/214 |
| 4,629,787 | 12/1986 | Harris et al. | 540/528 |
| 4,680,392 | 7/1987 | Harris et al. | 540/527 |
| 4,699,905 | 10/1987 | Yanagisawa et al. | 514/211 |
| 4,711,884 | 12/1987 | Karanewsky | 514/226 |
| 4,722,810 | 2/1988 | Delaney et al. | 260/402.5 |
| 4,734,410 | 3/1988 | Yanagisawa et al. | 514/212 |
| 4,749,688 | 6/1988 | Haslanger et al. | 514/19 |
| 4,801,609 | 1/1989 | Haslanger et al. | 514/506 |
| 4,824,832 | 4/1989 | Flynn et al. | 514/214 |
| 4,873,235 | 10/1989 | Parsons et al. | 514/312 |
| 4,879,309 | 11/1989 | Doll et al. | 514/513 |
| 4,963,539 | 10/1990 | Delaney | 514/119 |
| 4,973,585 | 11/1990 | Flynn et al. | 514/214 |
| 5,061,710 | 10/1991 | Haslanger et al. | 514/266 |
| 5,075,302 | 12/1991 | Neustadt | 514/211 |
| 5,098,934 | 3/1992 | Vevert et al. | 514/513 |
| 5,190,974 | 3/1993 | Clemence et al. | 514/513 |
| 5,208,236 | 5/1993 | Neustadt | 514/237.5 |
| 5,223,516 | 6/1993 | Delaney et al. | 514/339 |
| 5,225,401 | 7/1993 | Seymour | 519/19 |
| 5,232,920 | 8/1993 | Neustadt | 514/212 |
| 5,238,924 | 8/1993 | Smith | 514/19 |
| 5,262,436 | 11/1993 | Haslanger et al. | 514/513 |
| 5,362,727 | 11/1994 | Robl | 514/214 |
| 5,366,973 | 11/1994 | Flynn et al. | 514/221 |
| 5,504,080 | 4/1996 | Karanewsky | 514/214 |
| 5,508,272 | 4/1996 | Robl | 514/80 |
| 5,525,723 | 6/1996 | Robl | 540/521 |
| 5,552,397 | 9/1996 | Karanewsky | 514/212 |

OTHER PUBLICATIONS

Robl et al., J. Am. Chem. Soc., 116, pp. 2348–2355 (1994).
Robl, Tetrahedron Letters, vol. 35, pp. 393–396 and 1393–1396 (1994).
Slade et al., J. Med. Chem., 28, pp. 1517–1521 (1985).
Smith et al., Biochemistry, vol. 14, pp. 766–771 (1975).
Thorsett et al., J. Med. Chem., 29, pp. 251–260 (1986).
Thorsett, Actual Chim. Ther., vol. 13, pp. 257–268 (1986).
Watthey et al., J. Med. Chem., 28, pp. 1511–1516 (1985).
Yanagisawa et al., J. Med. Chem., 30, pp. 1984–1991 (1987).
Yanagisawa et al., J. Med. Chem., 31, pp. 422–428 (1988).

DIAZEPINE CONTAINING DUAL ACTION INHIBITORS

RELATED APPLICATION

This application is a continuation-in-part of Ser. No. 474,041 filed on Jun. 7, 1995, now abandoned.

BACKGROUND OF THE INVENTION

Captopril, (S)-1-(3-mercapto-2-methyl-1-oxopropyl)-L-proline, having the structural formula

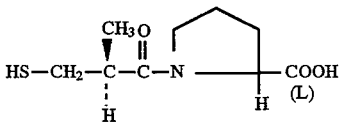

is an orally active angiotensin converting enzyme inhibitor useful for treating hypertension and congestive heart failure. See Ondetti et al. U.S. Pat. No. 4,105,776.

Enalapril, (S)-1-[N-[1-(ethoxycarbonyl)-3-phenylpropyl]-L-alanyl]-L-proline, having the structural formula

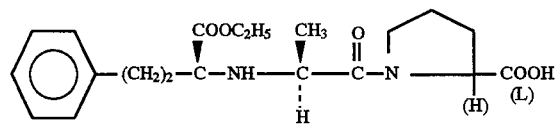

is also an orally active angiotensin converting enzyme inhibitor. Enalapril contains the L-alanyl-L-proline dipeptide. A related compound, lisinopril, also possesses oral angiotensin converting enzyme inhibitor activity and contains the L-lysyl-L-proline dipeptide. See Harris et al. U.S. Pat. No. 4,374,829.

Fosinopril sodium, (4S)-4-cyclohexyl-1-[[(R)-[(S)-1-hydroxy-2-methylpropoxy](4-phenylbutyl)-phosphinyl]acetyl]-L-proline propionate (ester), sodium salt having the structural formula

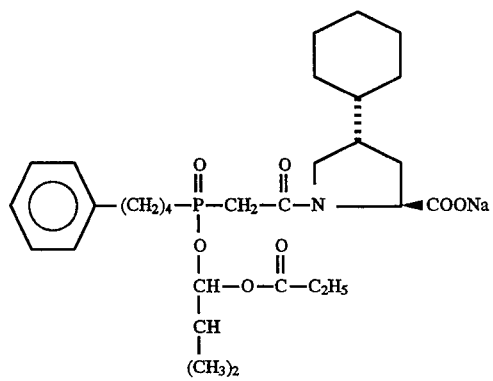

is also an orally active angiotensin converting enzyme inhibitor useful for treating hypertension. See Petrillo U.S. Pat. No. 4,337,201.

Haslanger et al., in U.S. Pat. No. 4,749,688, disclose treating hypertension by administering neutral metalloendopeptidase inhibitors alone or in combination with atrial peptides or angiotensin converting enzyme inhibitors.

Neustadt, in U.S. Pat. No. 5,075,302, discloses that mercaptoacyl amino lactams of the formula

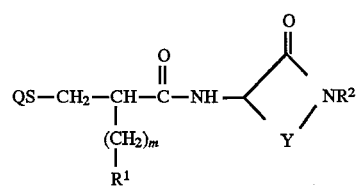

wherein Y includes propylene and butylene, $R^1$ is lower alkyl, aryl or heteroaryl, and $R^2$ is hydrogen, lower alkyl, lower alkoxy lower alkyl, aryl-lower alkyl or heteroaryl-lower alkyl are endopeptidase inhibitors. Neustadt discloses employing such compounds alone or in combination with angiotensin converting enzyme inhibitors to treat cardiovascular diseases such as hypertension, congestive heart failure, edema and renal insufficiency.

Delaney et al., in U.K. Patent 2,207,351, disclose that endopeptidase inhibitors produce diuresis and natriuresis and are useful alone or in combination with angiotensin converting enzyme inhibitors for the reduction of blood pressure. Delaney et al. include various mercapto and acylmercapto amino acids and dipeptides among their endopeptidase inhibiting compounds.

Flynn et al., in European Patent Application 481,522, disclose dual inhibitors of enkephalinase and angiotensin converting enzyme of the formulas

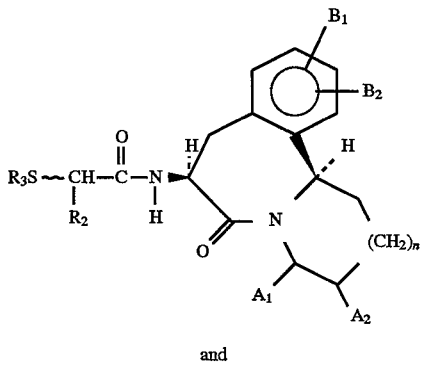

and

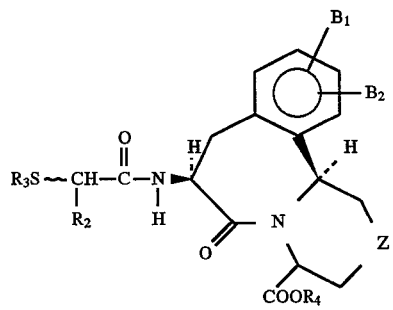

wherein n is zero or one and Z is O, S, —$NR_6$— or

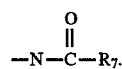

Additional tricyclic dual inhibitors are disclosed by Warshawsky et al. in European Patent Applications 534,363, 534,396 and 534,492.

Karanewsky et al., in U.S. Pat. Nos. 4,432,971 and 4,432,972, disclose phosphonamidate angiotensin converting enzyme inhibitors of the formula

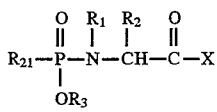

wherein X is a substituted imino or amino acid or ester.

Karanewsky, in U.S. Pat. No. 4,460,579, discloses angiotensin converting enzyme inhibitors including those of the formula

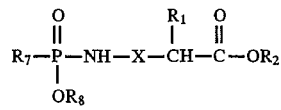

and, in U.S. Pat. No. 4,711,884, discloses angiotensin converting enzyme inhibitors including those of the formula

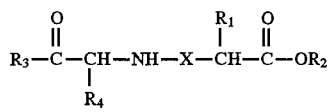

wherein X is a thiazine or thiazepine.

SUMMARY OF THE INVENTION

This invention is directed to novel compounds containing a diazepinone which are useful as angiotensin converting enzyme inhibitors. Some of these compounds possess neutral endopeptidase inhibitory activity as well. This invention is also directed to pharmaceutical compositions containing such selective or dual action inhibitors and to methods of using such compositions.

The novel diazepinone inhibitors of this invention include those compounds of the formula (I)

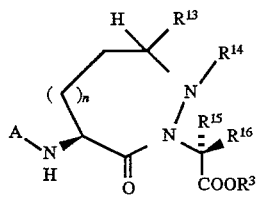

and pharmaceutically acceptable salts thereof wherein:

A is 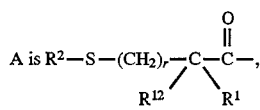

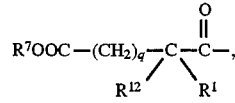

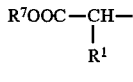

or

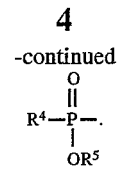

$R^1$ and $R^{12}$ are each independently selected from hydrogen, alkyl, alkenyl, cycloalkyl, substituted alkyl, substituted alkenyl, aryl, substituted aryl, heteroaryl, cycloalkyl-alkylene-, aryl-alkylene-, substituted aryl-alkylene- and heteroaryl-alkylene-, or $R^1$ and $R^{12}$ taken together with the carbon atom to which they are attached complete a cycloalkyl ring or a benzofused cycloalkyl ring.

$R^2$ is hydrogen,

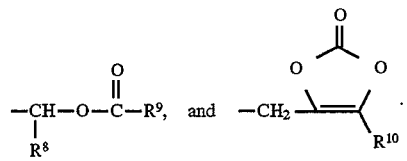

or $R_{11}$—S—

$R^3$, $R^5$ and $R^7$ are each independently selected from hydrogen, alkyl, substituted alkyl, aryl-$(CH_2)_p$—, substituted aryl-$(CH_2)_p$—, heteroaryl-$(CH_2)_p$—,

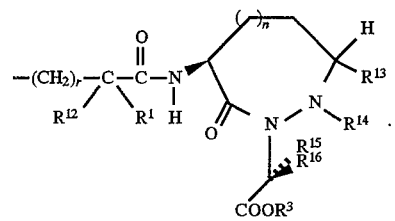

$R^4$ is alkyl, cycloalkyl-$(CH_2)_p$—, substituted alkyl, aryl-$(CH_2)_p$—, substituted aryl-$(CH_2)_p$— or heteroaryl-$(CH_2)_p$—.

$R^6$ is alkyl, substituted alkyl, cycloalkyl-$(CH_2)_p$—, aryl-$(CH_2)_p$—, substituted aryl-$(CH_2)_p$— or heteroaryl-$(CH_2)_p$—.

$R^8$ is hydrogen, lower alkyl, cycloalkyl or phenyl.

$R^9$ is hydrogen, lower alkyl, lower alkoxy or phenyl.

$R^{10}$ is lower alkyl or aryl-$(CH_2)_p$—.

$R^{11}$ is hydrogen, alkyl, substituted alkyl, cycloalkyl-$(CH_2)_p$—, aryl-$(CH_2)_p$—, substituted aryl-$(CH_2)_p$— or heteroaryl-$(CH_2)_p$—, or —S—$R^{11}$ completes a symmetrical disulfide wherein $R^{11}$ is $R^{13}$ is alkyl, aryl, or aryl-alkylene-.

$R^{14}$ is hydrogen, alkyl, aryl or aryl-alkylene- or $R^{13}$ and $R^{14}$ taken together are —$(CH_2)_3$— or —$(CH_2)_4$— thus completing a five- or six-membered ring.

$R^{15}$ and $R^{16}$ are each independently selected from hydrogen, alkyl, substituted alkyl, aryl and aryl-alkylene-.

n is zero or one.

p is zero or an integer from 1 to 6.

q is zero or an integer from 1 to 3.

r is zero or one.

DETAILED DESCRIPTION OF THE INVENTION

Listed below are definitions of terms used in this specification. These definitions apply to the terms as used throughout this specification, individually or as part of another group, unless otherwise limited in specific instances.

The term "alkyl" refers to straight or branched chain radicals having up to seven carbon atoms. The term "lower alkyl" refers to straight or branched radicals having up to four carbon atoms and is a preferred subgrouping for the term alkyl.

The term "substituted alkyl" refers to such straight or branched chain radicals of 1 to 7 carbons wherein one or more, preferably one, two, or three, hydrogens have been replaced by a hydroxy, amino, cyano, halo, trifluoromethyl, —NH(lower alkyl), —N(lower alkyl)$_2$, lower alkoxy, lower alkylthio or carboxy.

The expressions "lower alkoxy" and "lower alkylthio" refer to such lower alkyl groups as defined above attached to an oxygen or sulfur atom, respectively.

The term "cycloalkyl" refers to saturated rings of 3 to 7 carbon atoms with cyclopropyl, cyclobutyl, cyclopentyl and cyclohexyl being most preferred.

The term "alkenyl" refers to straight or branched chain radicals of 3 to 7 carbon atoms having one or two double bonds. Preferred "alkenyl" groups are straight chain radicals of 3 to 5 carbon atoms having one double bond.

The term "substituted alkenyl" refers to such straight or branched radicals of 3 to 7 carbon atoms having one or two double bonds wherein a hydrogen has been replaced by a hydroxy, amino, halo, trifluoromethyl, cyano, —NH(lower alkyl), —N(lower alkyl)$_2$, lower alkoxy, lower alkylthio or carboxy.

The term "alkylene" refers to straight or branched chain radicals having up to seven carbon atoms, i.e., —CH$_2$—, —(CH$_2$)$_2$—, —(CH$_2$)$_3$—, —(CH$_2$)$_4$—,

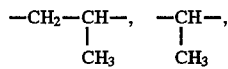

etc.

The term "aryl" refers to phenyl, 1-naphthyl, and 2-naphthyl. The term "substituted aryl" refers to phenyl, 1-naphthyl and 2-naphthyl having a substituent selected from lower alkyl, lower alkoxy, lower alkylthio, halo, hydroxy, trifluoromethyl, amino, —NH(lower alkyl) or —N(lower alkyl)$_2$, and di- and tri-substituted phenyl, 1-naphthyl or 2-naphthyl wherein said substituents are selected from methyl, methoxy, methylthio, halo, hydroxy and amino.

The term "heteroaryl" refers to unsaturated rings of 5 or 6 atoms containing one or two O and/or S atoms, and/or one to four N atoms, provided that the total number of heteroatoms in the ring is 4 or less. The heteroaryl ring is attached by way of an available carbon or nitrogen atom. Preferred heteroaryl groups include 2-, 3- or 4-pyridyl, 4-imidazolyl, 4-thiazolyl, 2- and 3-thienyl and 2- and 3-furyl. The term heteroaryl also includes bicyclic rings wherein the five or six membered ring containing O, S and/or N atoms as defined above is fused to a benzene or pyridyl ring. Preferred bicyclic rings are 2- and 3-indolyl and 4- and 5-quinolinyl. The mono or bicyclic heteroaryl ring can also be additionally substituted at an available carbon atom by a lower alkyl, halo, hydroxy, benzyl or cyclohexylmethyl. Also, if the mono or bicyclic ring has an available N atom, such N atom can also be substituted by an N-protecting group such as

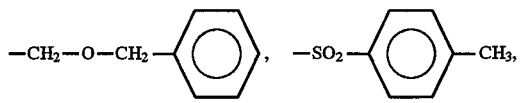

2,4-dinitrophenyl, lower alkyl, benzyl or benzhydryl.

The term "halo" refers to fluoro, chloro, bromo and iodo.

The compounds of formula I wherein A is

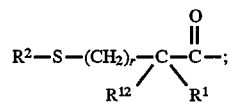

R$^2$ is hydrogen; R$^{13}$ is alkyl, aryl, or aryl-alkylene-; and R$^{14}$ is hydrogen, alkyl, aryl or aryl-alkylene- can be prepared, for example, by the general route as shown below in Scheme 1:

Scheme 1

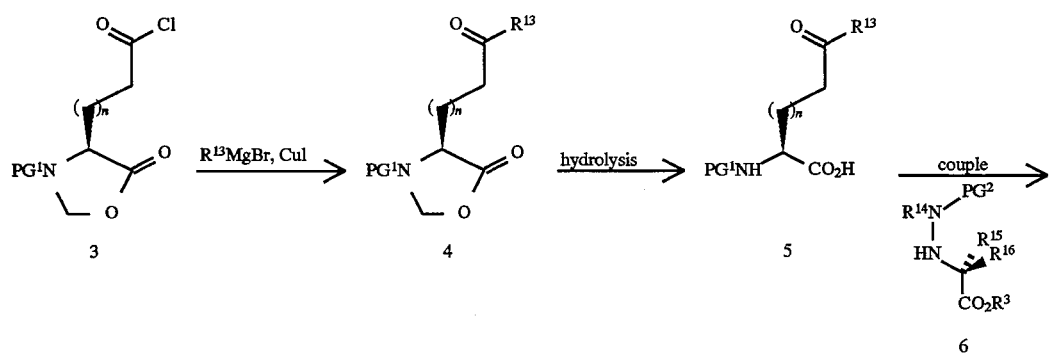

-continued
Scheme 1

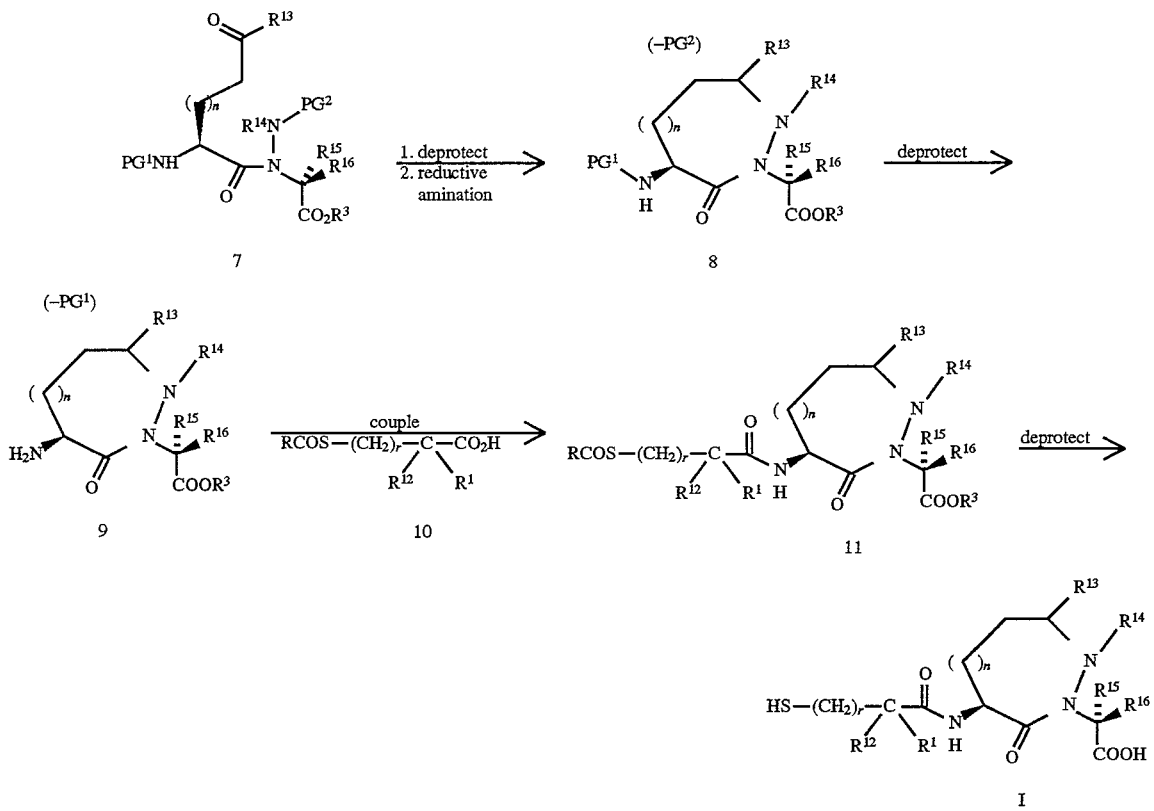

Following the scheme, the cuprous halide catalyzed condensation of an organometallic reagent (for example, a Grignard reagent) with a suitably protected acid chloride 3 gives a ketone 4. Compounds of type 3 may be derived from methods described in the literature as known to those skilled in the art. A preferred protecting group (PG) for the $PG^1$ position is benzyloxycarbonyl (Cbz).

Selective "hydrolysis" of the ketone 4 (with, for instance, sodium hydroxide and methanol) provides an acid 5.

Coupling of the acid 5 with a suitably protected N-azaglycine derivative 6 gives a compound 7. (For example, the acid 5 can be treated with cyanuric fluoride and pyridine. An acid fluoride forms and reacts with the suitably protected N-azaglycine derivative 6 in the presence of 2,6-di-t-butylpyridine to afford compound 7.) N-Azaglycine derivatives 6 may be prepared from methods described in the literature as known to those skilled in the art. A preferred protecting group for the N-azaglycine derivatives ($PG^2$) is t-butoxycarbonyl (BOC).

Selective "deprotection" (for example with hydrochloric acid and dioxane when $PG^2$ is BOC) of compound 7, followed by reductive amination (with, for example, sodium cyanoborohydride ($NaBH_3CN$), 1% acetic acid/ethanol) affords compound 8.

Selective deprotection of compound 8 (with hydrogen, palladium on carbon or iodotrimethylsilane (TMSI) when $PG^1$ is a Cbz group) gives an amine 9. Coupling of the amine 9 to acid 10 (with benzotriazol-1-yloxytris(dimethylamino) phosphonium hexafluorophosphate (BOP reagent), triethylamine (TEA) and methylene chloride) provides compound 11. Finally, deprotection of compound 11 affords the compound of formula I as discussed above.

Compounds of formula I wherein $R^3$ is other than hydrogen can be prepared by reacting intermediate 11 in a suitable solvent or solvent mixture, such as acetonitrile and methanol, with mercuric trifluoroacetate at room temperature. Upon complete disappearance of the starting material, the reaction mixture is treated briefly with gaseous hydrogen sulfide and filtered to remove the black precipitate of mercuric sulfide. The desired product is isolated by the usual means.

The compounds of formula I wherein A is

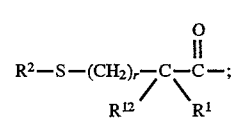

$R^2$ is hydrogen; and $R^{13}$ and $R^{14}$ taken together are $—(CH_2)_3—$ or $—(CH_2)_4—$ thus completing a five- or six-membered ring can be prepared, for example, by the general route as shown below in Scheme 2.

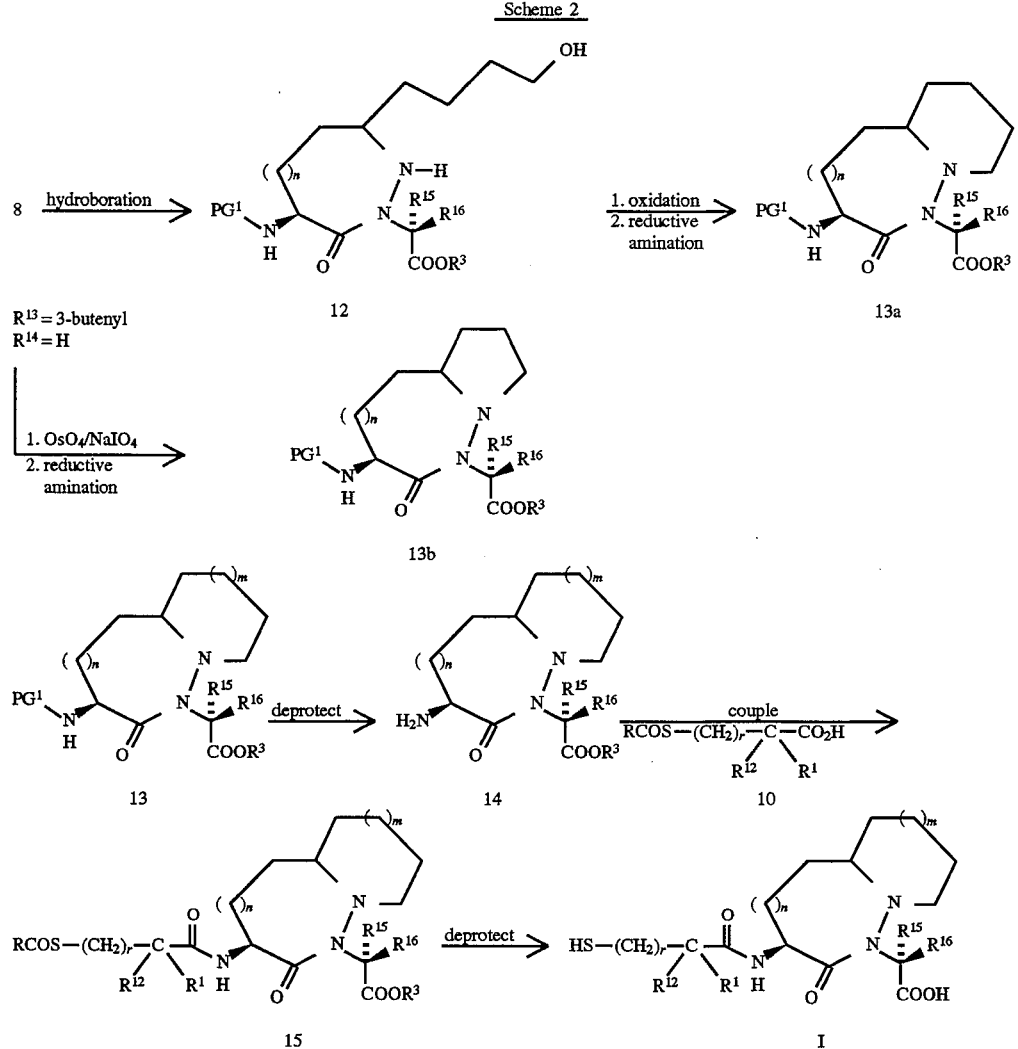

Following Scheme 2, hydroboration of compound (prepared as discussed above), where $R^{13}$ is 3-butenyl and $R^{14}$ is hydrogen, gives an alcohol 12. Oxidation of the alcohol 12, followed by reductive amination (for example with NaBH$_3$CN and 1% acetic acid/ethanol) affords the bicyclic compound 13a. Conversely, oxidative cleavage (with, for example, osmium tetraoxide (OsO$_4$)/sodium periodate (NaIO$_4$)) of compound 8, followed by reductive amination (e.g., with NaBH$_3$CN and 1% acetic acid/ethanol) gives the bicyclic compound 13b. A preferred protecting group for PG$^1$ is Cbz. Selective deprotection of 13 (a or b) (with hydrogen, palladium on carbon or TMSI when PG$^1$ is a Cbz group) gives an amine 14. Coupling of amine 14 to acid 10 (from Scheme 1), for example with BOP reagent, TEA and methylene chloride, provides compound 15. Finally, deprotection of compound 15 affords a compound of formula I as discussed above. Note that m in formulas 13, 14, 15 and 1 is either zero or one.

The products of formula I from Scheme 1 or Scheme 2, wherein $R^2$ is hydrogen, can be acylated with an acyl halide of the formula

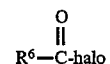

wherein halo is F, Cl or Br, or acylated with an anhydride of the formula

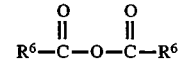

to give other products of formula I wherein $R^2$ is

The products of formula I wherein $R^2$ is —S—$R^{11}$, and $R^{11}$ is alkyl, substituted alkyl, cycloalkyl-(CH$_2$)$_p$—, aryl-(CH$_2$)$_p$—, substituted aryl-(CH$_2$)$_p$— or heteroaryl-(CH$_2$)$_p$—, can be prepared by reacting the products of formula I from Scheme 1 or Scheme 2, wherein $R_2$ is hydrogen, with a sulfonyl compound of the formula

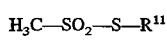

in an aqueous alcohol solvent to yield the desired products. The sulfonyl compounds of the formula $H_3C-SO_2-S-R^{11}$ are known in the literature or can be prepared by known methods. See, for example, Smith et al., Biochemistry, 14, p 766–771 (1975).

The products of formula I wherein $R^2$ is SH can be prepared by reacting the product of formula I from Scheme 1 or Scheme 2, wherein $R^2$ is hydrogen, with a sulfonyl compound of the formula $H_3C-SO_2-S-R^{11}$ wherein $R^{11}$ is triphenylmethyl or trialkylsilyl followed by removal of the triphenylmethyl or trialkylsilyl group under acidic conditions.

The symmetrical disulfide products of formula I can be prepared by direct oxidation of the product of formula I from Scheme 1 or Scheme 2, wherein $R^2$ is hydrogen, with iodine according to known procedures. See, for example, Ondetti et al. U.S. Pat. No. 4,105,776.

The acylmercapto sidechain compounds 10 wherein $R^{12}$ is hydrogen are described in the literature. See, for example, Ondetti et al. U.S. Pat. Nos. 4,105,776 and 4,339,600, Haslanger et al. U.S. Pat. No. 4,801,609, Delaney et al. U.S. Pat. No. 4,722,810, etc.

The acylmercapto sidechain compounds 10 wherein $R^1$ and $R^{12}$ are both other than hydrogen and r is zero can be prepared by reacting the substituted carboxylic acid of the formula

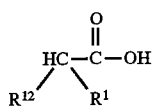

with bis[(4-methoxy)phenyl]methyldisulfide in the presence of lithium diisopropylamide to give the compound of the formula

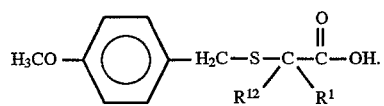

Treatment of this compound with strong acid such as trifluoromethanesulfonic acid removes the methoxybenzyl protecting group and is followed by acylation with the acyl halide of the formula

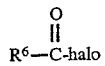

(above) or the anhydride of the formula

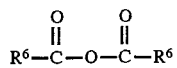

(above) to give compound 10 wherein $R^1$ and $R^{12}$ are both other than hydrogen and r is zero.

Alternatively, the substituted carboxylic acid of the formula

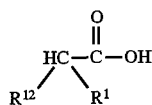

(above) can be reacted with lithium diisopropylamide and sulfur to give the mercaptan of the formula

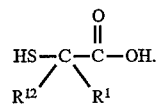

This mercaptan can then be acylated with the acyl halide of the formula

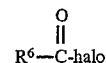

(above) or the anhydride of the formula

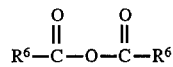

(above) to give compound 10 wherein $R^1$ and $R^{12}$ are both other than hydrogen and r is zero.

The acylmercapto sidechain compound 10 wherein $R^1$ and $R^{12}$ are both other than hydrogen and r is one can be prepared by reacting the substituted carboxylic acid of the formula

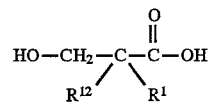

with para-toluenesulfonyl chloride in pyridine to give the lactone of the formula

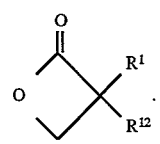

Treatment of this lactone with a cesium thioacid of the formula

in the presence of dimethylformamide yields the desired acylmercapto sidechain of compound 10 wherein $R^1$ and $R^{12}$ are both other than hydrogen and r is one.

Compounds of formula I wherein A is

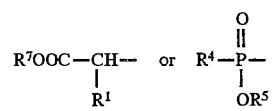

may be prepared from the corresponding amines 9 and 14 above using chemistry described in the literature as known to those skilled in the art.

Compounds of formula I wherein A is

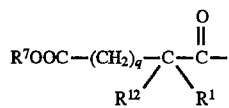

can be prepared by coupling the acid of the formula

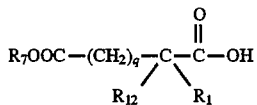

wherein $R_7$ is an acid protecting group with the amine 9 or 14 in the presence of a coupling reagent such as defined above. Alternatively, the acid of formula 16 can be converted to an activated form such as an acid chloride prior to the coupling reaction.

The acids of formula 16 are described by Warshawsky et al. in European Patent Application 534,396 and 534,492.

While the optically pure form of the compounds of formula I described above is preferred, all forms of the compounds are within the scope of this invention. The above described processes can utilize racemates, enantiomers, or diastereomers as starting materials. When diastereomeric compounds are prepared, they can be separated by conventional chromatographic or fractional crystallization methods.

The compounds of formula I where possible can be isolated in the form of a pharmaceutically acceptable salt. Suitable salts for this purpose are alkali metal salts such as sodium and potassium, alkaline earth metal salts such as calcium and magnesium, salts derived from amino acids such as arginine, lysine, etc. and salts derived from amines such as alkyl amines, e.g., t-butylamine, t-amylamine, etc., substituted alkylamines, e.g., benzylamine, dialkylamines, substituted dialkylamines, e.g., N-methyl glucamine, trialkylamines, substituted trialkylamines, and quaternary ammonium salts. These salts can be obtained by reacting the acid form of the compound with a base supplying the desired ion in a medium in which the salt precipitates or in aqueous medium and then lyophilizing.

Preferred compounds of this invention are those wherein:

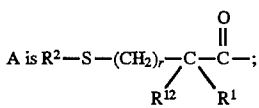

$R^1$, $R^2$ and $R^3$ are each hydrogen;

$R^{12}$ is benzyl;

$R^{13}$ is alkyl; especially butyl;

$R^{14}$ is hydrogen or $R^{13}$ and $R^{14}$ taken together are $-(CH_2)_3-$ or $-(CH_2)_4-$ thus completing a five- or six-membered ring;

n is one; and r is zero.

The compounds of formula I wherein A is

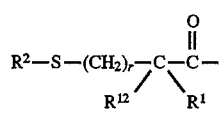

-continued
or

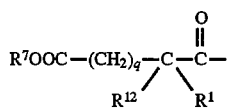

are dual inhibitors possessing the ability to inhibit angiotensin converting enzyme and neutral endopeptidase. The compounds of formula I wherein A is

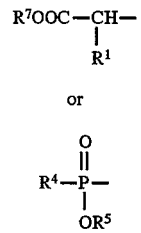

are selective inhibitors possessing the ability to inhibit the angiotensin converting enzyme. Thus, the compounds of formula I, including their pharmaceutically acceptable salts, are useful in the treatment of physiological conditions in which angiotensin converting enzyme inhibitors have been shown to be useful. Such conditions include disease states characterized by abnormalities in blood pressure, intraocular pressure and renin including cardiovascular diseases particularly hypertension and congestive heart failure, glaucoma and renal diseases such as renal failure, diabetic nephropathy and renal impairment following treatment with cyclosporine or other immunosuppressants. Other conditions in which angiotensin converting enzyme inhibitors have been reported to be useful include hepatic cirrhosis, inhibiting the progression of atherosclerosis, preventing or treating hypertensive or diabetic retinopathy, improving myocardial dysfunction during or following a myocardial infarction and preventing restinosis after angioplasty. The dual inhibitors are also useful in the treatment of physiological conditions in which neutral endopeptidase inhibitors have been shown to be useful. Such conditions also include cardiovascular diseases particularly hypertension, hyperaldosteronemia, renal diseases and glaucoma, as well as the relief of acute or chronic pain. Thus, the compounds of formula I are useful in reducing blood pressure and the dual inhibitors of formula I are additionally useful for this purpose due to their diuresis and natriuresis properties. The dual inhibitors are particularly useful in the treatment of congestive heart failure.

The compounds of formula I, including pharmaceutically acceptable salts thereof, can be administered for these effects in amounts similar to those employed previously for angiotensin converting enzyme inhibitors. For example, the compounds of formula I can be administered to a mammalian host such as man at from about 0.1 mg to about 100 mg per kg of body weight per day, preferably from about 0.5 mg to about 25 mg per kg of body weight per day. The compounds of formula I are preferably administered orally but parenteral routes such as subcutaneous, intramuscular and intravenous can also be employed, as can topical routes of administration. The daily dose can be administered singly or it can be divided into two to four doses administered throughout the day.

The inhibitors of formula I can be administered in combination with human ANF (atrial natriuretic factor) 99–126. Such combination would contain the inhibitor of formula I at from about 1 to about 100 mg per kg of body weight, and the human ANF 99–126 at from about 0.001 to about 0.1 mg per kg of body weight.

The inhibitors of formula I can be administered in combination with other classes of pharmaceutically active compounds. For example, they can be administered with a diuretic, a calcium channel blocker, a potassium channel activator, a cholesterol reducing agent, a β-blocker, an angiotensin II antagonist, etc.

The inhibitors of formula I or a pharmaceutically acceptable salt thereof and other pharmaceutically acceptable ingredients can be formulated for the above described pharmaceutical uses. Suitable compositions for oral administration include tablets, capsules and elixirs, and suitable compositions for parenteral administration include sterile solutions and suspensions. Suitable compositions for treating glaucoma also include topical compositions such as solutions, ointments, and solid inserts as described in U.S. Pat. No. 4,442,089. About 10 to 500 mg of active ingredient is compounded with physiologically acceptable vehicle, carrier, excipient, binder, preservative, stabilizer, flavoring, etc., in a unit dose form as called for by accepted pharmaceutical practice.

The following examples are illustrative of the invention. Temperatures are given in degrees centigrade. Thin layer chromatography (TLC) was performed in silica gel unless otherwise stated.

EXAMPLE 1

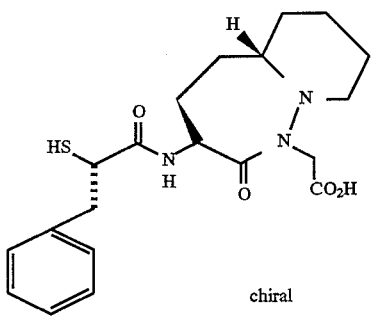

chiral

[3S-[3α(R*),5aα]]-Decahydro-3-[(2-mercaoto-1-oxo-3-phenylpropyl)amino]-2-oxopyrido[1,2-b][1,2] diazepine-1-acetic acid A. 2-(2-Ethoxy-2-oxoethyl)hydrazinecarboxylic acid, 1,1-dimethylethyl ester A 500 mL 3-neck round bottom flask was charged with t-butyl carbazate (15.0 g, 113.5 mmol), toluene (120 mL), triethylamine (18.98 mL, 136.2 mmol) and ethyl bromoacetate (15.10 mL, 136.2 mmol). The mixture was heated in an oil bath to about 100° C. for 19 hours. The reaction mixture was allowed to cool to room temperature and was then filtered, washing the solid triethylamine bromide with ethyl acetate/hexanes. The combined organics were washed successively with saturated sodium bicarbonate, water and brine, dried over sodium sulfate, filtered, concentrated and dried in vacuo to give a crude reddish oil (20.78 g). The crude material was absorbed onto Celite® and purified on a 10×20 cm silica gel column eluting with 15% (4 L), 20% (7 L), 30% (2 L), 40% (2 L), 50% (2 L) ethyl acetate/hexanes and finally ethyl acetate (2 L). The desired fractions were combined and concentrated to give an oil (10.85 g) which solidified upon standing. The residue was concentrated with dichloro-methane/toluene and dried in vacuo to give compound A (44%) as an off-white solid. TLC: $R_f$=0.13, silica gel, 30% ethyl acetate/hexanes, UV and PMA detection.

B. (S)-5-Oxo-3-[(phenylmethoxy)carbonyl]-4-oxazolidinepropanoic acid

A 2 L 3-neck round bottom flask fitted with a Dean-Stark trap and a condenser was charged with (S)-2-[(phenylmethoxy)carbonyl]amino]pentanedioic acid (50 g, 177.75 mmol), paraformaldehyde (9.07 g, 302.18 mmol) and p-toluenesulfonic acid monohydrate (1.69 g, 8.89 mmol) in toluene (800 mL). The suspension was stirred and then refluxed for 6.5 hours. The brown solution that formed was allowed to cool to room temperature overnight. The reaction mixture was washed with water (500 mL) and 10% sodium bicarbonate (2×500 mL). The combined sodium bicarbonate aqueous washes were cooled to 0° C. and acidified to pH 2 with 6N hydrochloric acid. The acidic aqueous mixture was extracted with ethyl acetate (2×500 mL), dried over sodium sulfate, filtered, concentrated and dried in vacuo to give compound B as a yellow oil (40 g, 77%).

C. (S)-4-(3-Chloro-3-oxopropyl)-5-oxo-3-oxazolidinecarboxylic acid, phenylmethyl ester Compound B (13.45 g, 45.86 mmol) was stripped with toluene three times, and dried in vacuo for 1 hour and then diluted with 50 mL anhydrous dichloromethane (distilled from calcium hydride ($CaH_2$)). The solution was treated with a few drops of anhydrous dimethylformamide, followed by dropwise addition of thionyl chloride (4.00 mL, 55.03 mmol), and stirred at room temperature under argon for 2 hours. The volatiles were removed in vacuo and the oily residue was triturated with ethyl ether. The resulting solid was collected under nitrogen umbrella, washed well with ethyl ether and dried in vacuo overnight to give 8.31 g of compound C (58%) as a white solid.

D. (S)-5-Oxo-4-(3-oxo-6-heptenyl)-3-oxazolidinecarboxylic acid, phenylmethyl ester A 100 mL 3-neck flask equipped with a condenser, a magnetic stir-bar and an addition funnel was charged with magnesium turnings (798 mg). The flask and magnesium were flame dried and cooled to room temperature under argon. The magnesium was then treated with anhydrous tetrahydrofuran (12 mL) and 0.5 mL of a solution of 4-bromo-1-butene (2.73 mL, 26.86 mmol, 1.8 eq) in anhydrous tetrahydrofuran (3 mL). Once the exothermic reaction began, the remainder of the 4-bromo-1-butene was added over 15 minutes to the flask cooled with an ice-bath. The ice-bath was removed and the thick grey slurry was refluxed for 1.5 hours and then allowed to cool to room temperature.

A 250 mL 3-neck flask equipped with a stir bar and an addition funnel flame dried and cooled under argon was charged with compound C (4.62 g, 14.92 mmol), anhydrous tetrahydrofuran (30 mL) and copper iodide (142 mg, 0.746 mmol). The suspension was stirred and cooled to –20° C. (carbon tetrachloride/dry ice bath). The Grignard formed above was cannulated dropwise into the reaction mixture over a period of 1 hour maintaining internal temperature at no higher than –10° C. The reaction mixture was stirred at –15° C. for 1.5 hours and then quenched with saturated ammonium chloride solution. The mixture was diluted with ethyl acetate and water, and the separated aqueous phase was extracted again with ethyl acetate. The combined ethyl acetate extracts were washed with brine, dried over sodium sulfate, filtered and concentrated to give an oil (5.38 g). The residue was absorbed onto Celite® and purified on a 5×25 cm silica gel column, eluting with 15% (3 L), 20% (2 L), and 30% (2 L) ethyl acetate/hexanes. The desired fractions were combined, concentrated and dried in vacuo to yield 3.23 g (67%) of compound D. TLC: $R_f$=0.54 silica gel; 1:1 ethyl acetate:hexanes; UV and PMA detection.

E. (S)-5-Oxo-2-[[(phenylmethoxy)carbonyl]amino]-8-nonenoic acid

A solution of compound D (3.97 g, 11.98 mmol) in methanol (40 mL) was treated with 13.2 mL of 1N sodium hydroxide. The mixture was vigorously stirred overnight at room temperature. The volatiles were removed in vacuo, and the reaction mixture was diluted with water, acidified to pH 2 with 1N hydrochloric acid and extracted with ethyl acetate (3×100 mL). Combined ethyl acetate extracts were washed with brine, dried over sodium sulfate, filtered and concentrated to yield a crude oil (5.31 g) that was absorbed onto Celite® and purified on a 5×15 cm silica gel column eluting with 1:1 ethyl acetate:hexanes (500 mL), 7:3 ethyl acetate:hexanes+0.3% acetic acid (2 L), 8:2 ethyl acetate:hexanes+ 0.5% acetic acid, and finally 8:2 ethyl acetate:hexanes+1% acetic acid (2 L). The desired fractions were combined, concentrated and dried in vacuo to afford 1.67 g (44%) of compound E as an oil. TLC: $R_f$=0.40 silica gel; 1% acetic acid in ethyl acetate; UV and PMA.

F. (S)-N-[[(1,1-Dimethylethoxy)carbonyl]amino]-N-(2-ethoxy-2-oxoethyl)-5-oxo-2-[[(phenylmethoxy)carbonyl]amino]-8-nonenamide Compound E (1.66 g, 5.20 mmol), azeotroped with toluene (3 times) and dried in vacuo, was dissolved in anhydrous dichloromethane (20 mL) and cooled to −12° C. (acetone/ice bath). The solution was treated with pyridine (845 µL, 10.40 mmol) followed by cyanuric fluoride (937 µL, 10.40 mmol). After stirring at −10° C. for one hour (yellow suspension formed in 10 minutes), crushed ice and dichloromethane were added and the layers separated. The aqueous layer was extracted again with dichloromethane. The combined dichloromethane layers were washed with ice-cold water, dried over magnesium sulfate, concentrated, azeotroped with toluene (three times) and dried in vacuo for one hour to afford acid fluoride (1.55 g) as a yellow oil.

The above acid fluoride was added to anhydrous dichloromethane (10 mL) followed by compound A (1.36 g, 6.24 mmol) and 2,6-di-tert-butylpyridine (1.40 mL, 6.24 mmol) at 0° C. The reaction mixture was stirred at 0° C. for 30 minutes and then at room temperature overnight. The reaction mixture was concentrated in vacuo, diluted with ethyl acetate (150 mL) and washed with 5% potassium bisulfate (100 mL) and brine (100 mL), dried over magnesium sulfate, filtered and concentrated. The residue was absorbed onto Celite® and purified on a 5×20 cm silica gel column eluting with 25% ethyl acetate/hexanes (4 L). The desired fractions were combined, concentrated and dried in vacuo to yield 2.19 g of compound F as an oil. TLC: $R_f$=0.40 silica gel; 30% ethyl acetate/hexanes; UV and PMA detection.

G. (S)-3-(3-Butenyl)-4,5,6,7-tetrahydro-7-oxo-6-[[(phenylmethoxy)carbonyl]amino]-1H-1,2-diazepine-1-acetic acid, ethyl ester To a solution of compound F (2.19 g, 4.21 mmol) in anhydrous dichloromethane (40 mL, distilled from CaH$_2$) cooled to 0° C. was added 4.0M (HCl/dioxane (10 mL). The reaction was stirred at 0° C. for 30 minutes and then at 5° C. overnight. The reaction mixture was concentrated in vacuo, diluted with ethyl acetate (150 mL), washed with saturated sodium bicarbonate solution (75 mL), water (75 mL) and brine (75 mL), dried over magnesium sulfate, filtered, and concentrated. The crude residue was absorbed onto Celite® and purified on a 5×20 cm silica gel column eluting with 20% (5 L) and 25% (2 L) ethyl acetate/hexanes. The desired fractions were combined, concentrated and dried in vacuo to afford 1.16 g of Compound G as an oil. TLC: $R_f$=0.41 silica gel; 1:1 ethyl acetate:hexanes; UV and PMA detection.

H. (3S-trans)-3-(3-Butenyl)hexahydro-7-oxo-6-[[(phenylmethoxy)carbonyl]amino]-1H-1,2-diazepine-1-acetic acid, ethyl ester To a solution of compound G (893 mg, 2.22 mmol) in 1% acetic acid in ethanol (20 mL) was added sodium cyanoborohydride (1.40 g, 21.56 mmol, in 8 portions, about one portion per hour). After 8 hours, the reaction was quenched with saturated sodium bicarbonate solution at 0° C. and then concentrated in vacuo. The white residue was extracted three times with ethyl acetate and the combined ethyl acetate extracts were washed with 50% brine, dried over MgSO$_4$, filtered and concentrated to give an oil (950 mg). The residue was absorbed onto Celite® and purified on a 5×20 cm silica gel column eluting with 20% (3 L), 30% (1 L) and 40% (1 L) ethyl acetate/hexanes. The desired fractions were combined, concentrated and dried in vacuo to afford 690 mg (77%) of compound H as an oil. TLC: $R_f$=0.56 silica gel; 1:1 ethyl acetate:hexanes; UV and PMA active. Compound H solidified upon standing and was recrystallized from hot ethyl acetate/hexanes.

I. (3S-trans)-Hexahydro-3-(4-hydroxybutyl)-7-oxo-6-[[(phenylmethoxy)carbonyl]amino]-1H-1,2-diazepine-1-acetic acid, ethyl ester To a solution of compound H (334 mg, 0.83 mmol) in anhydrous tetrahydrofuran (4 mL) was added 9-borabicyclo[3,3,1]nonane (9-BBN) (3.5 mL, 1.75 mmol, 0.5M solution in tetrahydrofuran) dropwise at room temperature under argon. After 30 minutes, additional 9-BBN (3.5 mL) was added and the mixture was stirred at room temperature. After 1.5 hours, still more 9-BBN (1.1 mL, 0.55 mmol) was added and the mixture was stirred at room temperature under argon for 30 minutes. The reaction was cooled to 0° C., 3N NaOH (1 mL) was added followed by 30% H$_2$O$_2$ (1 mL) and the mixture was stirred at 0° C. for 30 minutes and then at room temperature for 30 minutes. The reaction was concentrated in vacuo, partitioned between ethyl acetate and water, and the separated aqueous phase was extracted with ethyl acetate (twice). The combined ethyl acetate extracts were washed with water and brine, dried over magnesium sulfate, filtered, concentrated, absorbed onto Celite® and purified on a 5×20 cm silica gel column eluting with 60% ethyl acetate/hexanes. The desired fractions were combined, concentrated and dried in vacuo to afford 244 mg (70%) of compound I as an oil. TLC: $R_f$=0.31 silica gel; 8:2 ethyl acetate:hexanes; UV and PMA detection.

J. (3S-cis)-Decahydro-2-oxo-3-[[(phenylmethoxy)carbonyl]amino]pyrido[1,2-b][1,2]diazepine-1-acetic acid, ethyl ester To anhydrous dichloromethane (2 mL) cooled to −78° C., under argon was added oxalyl chloride (384 µL, 0.767 mmol, 2.0M solution in dichloromethane) followed by dimethylsulfoxide (109 µL, 1.53 mmol) dropwise. After stirring at −78° C. for 5 minutes, compound I (231 mg, 0.548 mmol) in dichloromethane (3 mL) was added. The reaction mixture was stirred for 40 minutes at −78° C., and then triethylamine (336 µL, 2.41 mmol) was added dropwise. The reaction was warmed to −40° C. (acetonitrile/dry ice) and stirred at −40° C. for 30 minutes. The reaction was allowed to warm to room temperature and was diluted with ethyl acetate, washed with 5% potassium bisulfate, water and brine, dried over sodium sulfate, filtered and concentrated to give a crude yellow oil (215 mg). The crude oil was dissolved in 1% acetic acid in ethanol (5 mL) and treated with sodium cyanoborohydride (48 mg, 0.76 mmol). The reaction was stirred at room temperature for one hour and quenched with saturated sodium bisulfate solution. The reaction mixture was concentrated in vacuo, diluted with ethyl acetate, washed with saturated sodium bicarbonate solution, 50% brine and brine, dried over magnesium sulfate, and absorbed onto Celite®. The residue was purified on a 2.5×20 cm silica gel column eluting with 25% ethyl acetate/hexanes (2 L). The desired fractions were combined, concentrated and dried in vacuo to afford 214 mg (77% over two steps) of compound J as an oil. TLC: $R_f$=0.34 silica gel; 1:1 ethyl acetate:hexanes; UV and PMA detection.

K. (3S-cis)-3-Aminodecahydro-2-oxopyrido[1,2-b][1,2] diazepine-1-acetic acid, ethyl ester To a solution of compound J (214 mg, 0.53 mmol) in ethanol (5 mL) was added palladium hydroxide on carbon (45 mg). The suspension was purged (three times) with a vacuum aspirator/hydrogen and then stirred vigorously under hydrogen atmosphere at room temperature for 2 hours. The reaction mixture was filtered through a plug of Celite®, washing well with ethanol. The filtrate was concentrated and the residue was dried in vacuo to afford 149 mg of compound K as a crude oil. The residue was azeotroped with toluene (three times) and dried in vacuo overnight prior to use in next step.

L. (S)-2-(Acetylthio)benzenepropanoic acid

Sodium nitrite (10.3 g, 280 mmol) was added to a solution of D-phenylalanine (30.0 g, 181 mmol) and potassium bromide (73.5 g) in sulfuric acid (2.5N, 365 ml) over a period of one hour while maintaining the temperature of the reaction mixture at 0° C. The mixture was stirred for an additional hour at 0° C. and then for one hour at room temperature. The reaction solution was extracted with ether, the ether was back extracted with water, and the ether layer was dried over sodium sulfate. Ether was removed in vacuo, and distillation of the oily residue afforded 25.7 g of (R)-2-bromo-3-benzenepropanoic acid; b.p. 141° C. (0.55 mm of Hg); $[\alpha]_D$=+14.5° (c=2.4, chloroform).

A mixture of thioacetic acid (7 ml, 97.9 mmol) and potassium hydroxide (5.48 g, 97.9 mmol) in acetonitrile (180.5 ml) was stirred under argon at room temperature for 1¾ hours. The mixture was cooled in an ice-bath, and a solution of (R)-2-bromo-3-benzenepropanoic acid (20.4 g, 89 mmol) in acetonitrile (20 ml) was added over a ten minute period. The reaction was stirred under argon at room temperature for 5 hours and filtered, and the acetonitrile was removed in vacuo. The oily residue was dissolved in ethyl acetate and washed with 10% potassium bisulfate and water. Removal of the ethyl acetate in vacuo afforded 19.6 g of crude product. The crude product was purified via its dicyclo-hexylamine salt using isopropyl ether as solvent for crystallization. An analytical sample of (S)-2-(acetylthio) benzenepropanoic acid, dicyclohexylamine salt was prepared by recrystallization from ethyl acetate; m.p. 146°–147° C.; $[\alpha]_D$=−39.6° C. (c=1.39, chloroform).

Analysis calculated for $C_{11}H_{12}O_3S \cdot C_{12}H_{23}N$: C,68.11; H,8.70; N,3.45; S,7.91 Found: C,67.93; H,8.71; N,3.37; S,7.94.

M. [3S-[3α(R*),5aα]]-3-[[2-(Acetylthio)-1-oxo-3-phenylpropyl]amino]decahydro-2-oxopyrido[1,2-b][1,2] diazepine-1-acetic acid, ethyl ester A suspension of compound L (256.5 mg, 0.63 mmol) in ethyl acetate was washed with 5% potassium bisulfate (three times), water and brine, dried over magnesium sulfate, filtered, concentrated, stripped with dichloromethane (twice) and dried in vacuo overnight to give the free acid, (S)-α-(acetylthio)benzenepropanoic acid, as a crystalline solid (142 mg).

The free acid was dissolved in anhydrous dichloromethane (2 mL), cooled to 0° C. (ice bath) and treated with freshly distilled triethylamine (81 μL, 0.58 mmol), then compound K (142 mg, 0.53 mmol) in anhydrous dichloromethane (2 mL) and finally benzotriazol-1-yloxytris (dimethylamino)phosphonium hexafluorophosphate (279.7 mg, 0.63 mmol). The resultant solution was stirred at 0° C. for 1 hour then at room temperature for 4 hours. The reaction mixture was concentrated, diluted with ethyl acetate (50 mL), washed with 5% potassium bisulfate (20 mL), saturated sodium bicarbonate (20 mL), water (20 mL) and brine (20 mL), dried over magnesium sulfate, filtered and evaporated to dryness. The crude product (330 mg) was absorbed onto Celite® and chromatographed on a silica gel column (2.5×15 cm), eluting with 25% (2 L) ethyl acetate/hexane. The desired fractions were combined and concentrated, affording 209 mg of pure compound L. TLC: $R_f$=0.22 silica gel; 1:1 ethyl acetate:hexane; UV and PMA detection.

N. [3S-[3α(R*),5aα]]-Decahydro-3-[(2-mercapto-1-oxo-3-phenylpropyl)amino]-2-oxopyrido[1,2-b][1,2]diazepine-1-acetic acid A solution of L (209 mg, 0.44 mmol) in methanol (4 mL), purged with argon for 30 minutes and cooled to 0° C. was treated dropwise with a previously purged (argon, 30 minutes) solution of 1.0N sodium hydroxide (3 mL) maintaining the bubbling of argon throughout the addition and length of the reaction. The reaction mixture was stirred at 0° C. for 2 hours, acidified at 0° C. with 6N hydrochloric acid to pH 2 then extracted with ethyl acetate (3×30 mL). The combined organic extracts were washed with 50% brine (30 mL) and brine (30 mL), dried over sodium sulfate, filtered, and evaporated to dryness to give a white foam (200 mg). The residue was purified by chromatography on a 2.5×15 cm silica gel column eluting with 7:3 ethyl acetate:hexanes (400 mL) and 1% acetic acid in 7:3 ethyl acetate:heptane (1.5 L). The desired fractions were concentrated, stripped with dichloromethane/hexanes and dried in vacuo over phosphorus pentoxide at 50° C. overnight to yield 171 mg (96%) of the title compound as an amorphous white solid.

TLC: $R_f$=0.21 (1% acetic acid in ethyl acetate; UV and PMA detection), silica gel IR(KBr); 3449, 2936, 1734, 1638, 1456, 1213, 700 $cm^{-1}$.

$[\alpha]_D$=+25° (C 1.05, dichloromethane)

$^1$H-NMR: 300 MHz; $CDCl_3$: δ1.13–1.26(m, 3H), 1.40–1.80(m's, 6H), 2.02(d, 1H, J=8.82 Hz), 2.60(m, 2H), 2.70 (m, 1H), 3.00–3.20(m's, 2H), 3.25(m, 1H), 3.64(m, 1H), 3.94(d, 1H, J=17.3 Hz), 4.30 (d, 1H, J=17.3 Hz), 5.40 (m, 1H), 7.19–7.30(m, 5H), 7.54(d, 1H, J=7.04 Hz), 8.00 (broad s, 1H).

$^{13}$C-NMR: 75 MHz; $CDCl_3$: δ23.2, 23.6, 26.0, 28.7, 29.3, 41.1, 42.4, 44.3, 49.8, 50.3, 56.7, 126.8, 128.3, 129.3, 137.4, 171.5, 172.1, 173.4.

Analysis calculated for $C_{20}H_{27}N_3O_4S \cdot 0.23H_2O$: C, 58.65; H, 6.76; N, 10.26; S, 7.83. Found: C, 58.99; H, 6.90; N, 9.92; S, 7.59.

HPLC: $t_R$=13.26 min. K'=5.54 (97.7%, UV 220 nm); YMC S-30DS (C-18) 6.0×150 mm; 60% (B:A) Isocratic (A=90% water/methanol+0.2% phosphoric acid; B=90% methanol/water+0.2% phosphoric acid); flow rate at 1.5 mL/minute.

EXAMPLE 2

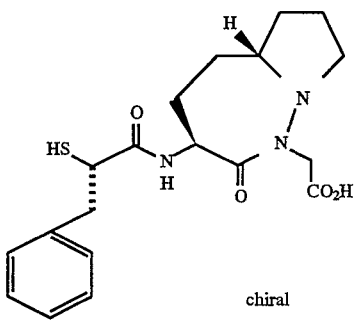

chiral

[3S-[3α(R*), 5aα]]-Octahydro-3-[(2-mercapto-1-oxo-3-phenyloropyl)amino]-2-oxo-1H-pyrrolo[1,2-b][1,2]diazeoine-1-acetic acid A. (3S-cis)-Octahydro-2-oxo-3-[[(phenylmethoxy)carbonyl]amino]-1H-pyrrolo[1,2-b][1,2]diazepine-1-acetic acid, ethyl ester To a solution of compound H from Example 1 above (605 mg, 1.50 mmol) in 2:1 tetrahydrofuran:water (6 mL) was added 2.5% weight solution of osmium tetroxide in 2-methyl-2-propanol (752 μL, 0.06 mmol) followed by a solution of N-methylmorpholine-N-oxide (263.4 mg, 2.24 mmol) in water (4 mL). The brown mixture was stirred overnight (15 hours) at room temperature under argon and then treated with a solution of sodium periodate (481 mg, 2.249 mmol) in water (4 mL). The reaction mixture was stirred at room temperature for 2 hours. The reaction mixture was diluted with ethyl acetate (40 mL) and water (30 mL) and the separated aqueous phase extracted with ethyl acetate (2×40 mL). The combined ethyl acetate extracts were washed with 50% brine and brine, dried over magnesium sulfate, filtered and concentrated to yield a crude black residue (547 mg).

The crude residue was dissolved in 1% acetic acid in ethanol (15 mL) and treated with sodium cyanoborohydride (141 mg, 2.249 mmol). The black mixture was stirred at room temperature under argon for one hour and then treated with more sodium cyanoborohydride (80 mg, 1.27 mmol). After one hour, the reaction was quenched with saturated sodium bicarbonate solution (1 mL), concentrated, and partitioned between a saturated sodium bicarbonate solution (40 mL) and ethyl acetate (40 mL). The separated aqueous phase was extracted with ethyl acetate (2×40 mL) and the combined ethyl acetate extracts were washed with 50% brine and brine, dried over magnesium sulfate, filtered and concentrated and absorbed onto Celite®. The residue was purified on a 5×15 cm silica gel column eluting with 35% ethyl acetate/hexanes (2 L). The desired fractions were combined, concentrated, stripped with dichloromethane (three times) and dried in vacuo to afford 508 mg (87%) of compound A as a clear oil. TLC: $R_f$=0.33 silica gel; 1:1 ethyl acetate:hexanes; UV and PMA detection.

B. (3S-cis)-3-Aminooctahydro-2-oxo-1H-pyrrolo[1,2-b][1,2]diazepine-1-acetic acid, ethyl To a solution of compound A (479 mg, 1.23 mmol) in ethanol (10 mL) was added palladium hydroxide on carbon (100 mg). The suspension was purged 6(three times) with a vacuum aspirator/hydrogen and then stirred vigorously under hydrogen atmosphere at room temperature for 1.5 hours. The reaction mixture was filtered through a plug of Celite®, washing well with ethanol. The filtrate was concentrated and the residue was dried in vacuo to afford 329 mg of compound B as a crude oil. Compound B was stripped with toluene (three times) and dried in vacuo to give a crystalline solid prior to use in the next step.

C. [3S-[3α(R*),5aα]]-3-[[2-(Acetylthio)-1-oxo-3-phenylpropyl]amino]octahydro-2-oxo-1H-pyrrolo[1,2-b][1,2]diazepine-1-acetic acid, ethyl ester A suspension of compound L from Example 1 (599 mg, 1.48 mmol) in ethyl acetate was washed with 5% potassium bisulfate (three times), water and brine, dried over magnesium sulfate, filtered, concentrated, stripped with dichloromethane (twice) and dried in vacuo for 2 hours to give the free acid, (S)-2-(acetylthio)benzene propanoic acid, as a crystalline solid.

The free acid was dissolved in anhydrous dichloromethane (5 mL), cooled to 0° C. (in an ice bath) and treated with freshly distilled triethylamine (189 μl, 1.35 mmol), then compound B (314 mg, 1.23 mmol) in anhydrous dichloromethane (5 mL) and finally BOP Reagent (653 mg, 1.48 mmol). The resultant solution was stirred at 0° C. for 1 hour and then at room temperature for 2.5 hours. The reaction mixture was concentrated, diluted with ethyl acetate (100 mL), washed with 5% potassium bisulfate (40 mL), saturated sodium bicarbonate (40 mL), 50% brine (40 mL) and brine (40 mL), dried over magnesium sulfate, filtered and evaporated to dryness. The crude product (680 mg) was absorbed onto Celite® and chromatographed on a silica gel column (5×15 cm), eluting with 35% (3 L) ethyl acetate/hexane. The desired fractions were combined and concentrated, and the residue was dried in vacuo to afford 499 mg (88% from Compound B) of pure compound C. TLC: $R_f$=0.29 silica gel; 1:1 ethyl acetate:hexane; UV and PMA detection.

D. [3S-[3α(R*),5aα]]-Octahydro-3-[(2-mercapto-1-oxo-3-phenylpropyl)amino]-2-oxo-1H-pyrrolo[1,2-b][1,2]diazepine-1-acetic acid A solution of compound C (469 mg, 1.02 mmol) in methanol (10 mL), purged with argon for 30 minutes and cooled to 0° C., was treated dropwise with a previously purged (argon, 30 minutes) solution of 1.0N sodium hydroxide (8 mL). The bubbling of argon was maintained throughout the addition and length of the reaction. The reaction mixture was stirred at 0° C. for 2 hours, acidified at 0° C. with 6N hydrochloric acid to pH 2 and then extracted with ethyl acetate (3×50 mL). The combined organic extracts were washed with 50% brine (50 mL) and brine (50 mL), dried over sodium sulfate, filtered, and evaporated to dryness to give a white foam (411 mg). The residue was chromatographed on a 5×15 cm silica gel column eluting with 7:3 ethyl acetate:hexanes (1 L) and 1% acetic acid in 7:3 ethyl acetate:heptane (3 L). The desired fractions were concentrated, stripped with ethyl acetate/hexanes and dried in vacuo over phosphorus pentoxide at 50° C. overnight to yield 345 mg (87%) of the title compound as an amorphous white solid.

TLC: $R_f$=0.23 (1% acetic acid in ethyl acetate; UV and PMA detection), silica gel.

IR(KBr); 3387, 2930, 2552, 1736, 1647, 1516, 1454, 1190, 700 cm$^{-1}$.

[α]$_D$=+12.6° (c 0.5, dichloromethane)

$^1$H-NMR: 400 MHz; CDCl$_3$: δ1.37–1.55(m, 2H), 1.70–2.00 (m's, 7H), 2.00(d, 1H, J=8.55 Hz), 2.90 (m, 1H), 3.08(m's, 2H), 3.26(m, 1H), 3.58(m, 1H), 4.03(d, 1H, J=17.1 Hz), 4.39 (d, 1H, J=17.1 Hz), 5.23 (m, 1H), 7.19–7.30(m, 5H), 7.41(d, 1H, J=6.84 Hz).

$^{13}$C-NMR: 75 MHz; CDCl$_3$: δ22.7, 29.8, 30.2, 34.5, 41.2, 43.8, 44.6, 49.9, 52.0, 58.4, 126.8, 128.3, 129.3, 137.5, 171.3, 172.2, 174.7.

Analysis calculated for $C_{19}H_{25}N_3O_4S.0.12H_2O$: C, 57.97; H, 6.46; N, 10.67; S, 8.14. Found: C, 58.10; H, 6.52; N, 10.54; S, 8.03.

HPLC: $t_R$=9.76 min. K'=3.84 (99.1%, UV 220 nm); YMC S-3ODS (C-18) 6.0×150 mm; 60% (B:A) Isocratic (A=90% water/methanol+0.2% phosphoric acid; B=90% methanol/water+0.2% phosphoric acid); flow rate at 1.5 mL/min.

EXAMPLE 3

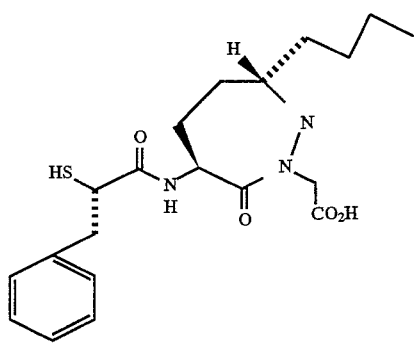

[3S-[3α, 6β(R*)]]-3-Butylhexahydro-6-[(2-mercapto-1-oxo-3-phenylpropyl)amino]-7-oxo-1H-1,2-diazepine-1-acetic acid A. (3S-trans)-6-Amino-3-butylhexahydro-7-oxo-1H-1,2-diazepine-1acetic acid, ethyl ester To a solution of compound H from Example 1 above (356 mg, 0.88 mmol) in ethanol (8 mL) was added palladium hydroxide on carbon (75 mg). The suspension was purged (three times) with a vacuum aspirator/hydrogen and then stirred vigorously under hydrogen atmosphere at room temperature for 2 hours. The reaction mixture was filtered through a plug of Celite®, washing well with ethanol. The filtrate was concentrated and the residue stripped with dichloromethane (three times) and dried in vacuo to afford 329 mg of compound A as a crude oil. Compound A was stripped with toluene (three times) and dried in vacuo to give a crystalline solid prior to use in the next step.

B. [3S-[3α,6β(R*)]]-6-[[2-(Acetylthio)-1-oxo-3-phenylpropyl]amino]-3-butylhexahydro-7-oxo-1H-1,2-diazepine-1-acetic acid, ethyl ester A suspension of compound L from Example 1 (427 mg, 1.05 mmol) in ethyl acetate was washed with 5% potassium bisulfate (three times), water and brine, dried over sodium sulfate, filtered, concentrated, stripped with dichloromethane (twice) and dried in vacuo overnight to give the free acid as a crystalline solid.

The free acid was dissolved in anhydrous dichtoromethane (4 mL), cooled to 0° C. (in an ice bath) and treated with triethylamine (134 μL, 0.96 mmol), then compound A (237 mg, 0.88 mmol) in anhydrous dichloromethane (5 mL) and finally BOP Reagent (465 mg, 1.05 mmol). The resultant solution was stirred at 0° C. for 1 hour and then at room temperature for 4 hours. The reaction mixture was concentrated, diluted with ethyl acetate (75 mL), washed with 5% potassium bisulfate (40 mL), saturated sodium bicarbonate solution (40 mL), 50% brine (40 mL) and brine (40 mL), dried over sodium sulfate, filtered, and evaporated to dryness. The crude product (462 mg) was absorbed onto Celite® and chromatographed on a silica gel column (5×10 cm), eluting with 30% (2 L) ethyl acetate/hexane. The desired fractions were combined and concentrated, affording 368 mg (87% from Compound H from Example 1) of pure Compound B. TLC: $R_f$=0.49 silica gel; 1:1 ethyl acetate:hexane; UV and PMA detection.

C. [3S-[3α,6β(R*)]]-3-Butylhexahydro-6-[(2-mercapto-1-oxo-3-phenylpropyl)amino]-7-oxo-1H-1,2-diazepine-1-acetic acid A solution of Compound B (469 mg, 1.02 mmol) in methanol (8 mL), purged with argon for 30 minutes and cooled to 0° C. was treated dropwise with a previously purged (argon, 30 minutes) solution of 1.0N sodium hydroxide (6 mL). The bubbling of argon was maintained throughout the addition and length of the reaction. The reaction mixture was stirred at 0° C. for 1 hour, allowed to warm to room temperature, and stirred for an additional 3 hours. The reaction mixture was then acidified at 0° C. with 6N hydrochloric acid to pH 2, and extracted with ethyl acetate (2×50 mL). The combined organic extracts were washed with 50% brine (50 mL) and brine (50 mL) dried over sodium sulfate, filtered and evaporated to dryness to give an oil (382 mg). The residue was chromatographed on a 2.5×20 cm silica gel column eluting with 7:3 ethyl acetate:hexanes (0.5 L) and 0.5% acetic acid in 7:3 ethyl acetate:heptane (2 L). The desired fractions were combined, concentrated, stripped with dichloromethane/hexanes and dried in vacuo over phosphorus pentoxide overnight to yield 287 mg (93%) of the title compound as an amorphous white solid.

TLC: $R_f$=0.12 (1% acetic acid in ethyl acetate; UV and PMA detection), silica gel.

IR(KBr); 3378, 2932, 2554, 1732, 1636, 1516, 1452, 1200, 700 cm$^{-1}$.

$[α]_D$=+18° (C 0.5, dichloromethane)

$^1$H-NMR: 400 MHz; CDCl$_3$: δ0.89(t, 3H, J=7.05 Hz), 1.20–1.70(m's, 8H), 1.91(m, 1H), 2.00(d, 1H, J=8.55 Hz), 2.07 (m, 1H), 2.71(m, 1H), 3.10(m, 1H), 3.27(m, 1H), 3.61(m, 1H), 4.05(d, 1H, J=17.1 Hz), 4.50 (d, 1H, J=17.1 Hz), 4.95 (m, 1H), 7.19–7.30(m, 5H), 7.51(d, 1H, J=5.99 Hz).

$^{13}$C-NMR: 75 MHz; CDCl$_3$: δ14.0, 22.5, 28.4, 30.0, 34.7, 34.8, 41.1, 44.4, 51.4, 52.2, 59.0, 126.9, 128.3, 129.3, 137.3,171.6, 172.2, 174.7.

Analysis calculated for $C_{20}H_{29}N_3O_4S$: C, 58.95; H, 7.17; N, 10.31; S, 7.87. Found: C, 58.97; H, 7.35; N, 10.18; S, 7.63.

HPLC: $t_R$=35.5 min. K'=16.89 (98.5%, UV 220 nm); YMC S-3ODS (C-18) 6.0×150 mm; 60% (B:A) Isocratic (A=90% water/methanol+0.2% phosphoric acid; B=90% methanol/water+0.2% phosphoric acid); flow rate at 1.5 mL/minute.

What is claimed is:
1. A compound of the formula

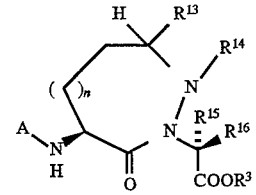

or a pharmaceutically acceptable salt thereof wherein:

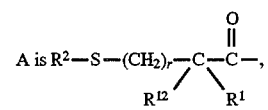

-continued

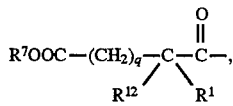

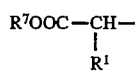

or

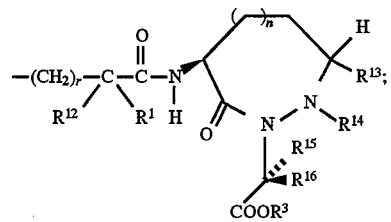

$R^1$ and $R^{12}$ are each independently selected from hydrogen, alkyl, alkenyl, cycloalkyl, substituted alkyl, substituted alkenyl, aryl, substituted aryl, heteroaryl, cycloalkyl-alkylene-, aryl-alkylene-, substituted aryl-alkylene- and heteroaryl-alkylene-, or $R^1$ and $R^{12}$ taken together with the carbon atom to which they are attached complete a cycloalkyl ring or a benzofused cycloalkyl ring;

$R^2$ is hydrogen,

or $R^{11}-S-$;

$R^3$, $R^5$ and $R^7$ are each independently selected from hydrogen, alkyl, substituted alkyl, aryl-$(CH_2)_p-$, substituted aryl-$(CH_2)_p-$, heteroaryl-$(CH_2)_p-$,

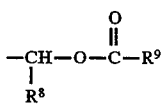

and

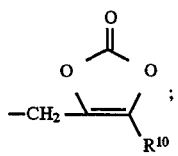

$R^4$ is alkyl, cycloalkyl-$(CH_2)_p-$, substituted alkyl, aryl-$(CH_2)_p-$, substituted aryl-$(CH_2)_p-$ or heteroaryl-$(CH_2)_p-$;

$R^6$ is alkyl, substituted alkyl, cycloalkyl-$(CH_2)_p-$, aryl-$(CH_2)_p-$, substituted aryl-$(CH_2)_p-$ or heteroaryl-$(CH_2)_p-$;

$R^8$ is hydrogen, lower alkyl, cycloalkyl or phenyl;

$R^9$ is hydrogen, lower alkyl, lower alkoxy or phenyl;

$R^{10}$ is lower alkyl or aryl-$(CH_2)_p-$;

$R^{11}$ is hydrogen, alkyl, substituted alkyl, cycloalkyl-$(CH_2)_p-$, aryl-$(CH_2)_p-$, substituted aryl-$(CH_2)_p-$ or heteroaryl-$(CH_2)_p-$, or $-S-R^{11}$ completes a symmetric wherein $R^{11}$ is $R^{13}$ is alkyl, aryl, or aryl-alkylene-;

$R^{14}$ is hydrogen, alkyl, aryl or aryl-alkylene- or $R^{13}$ and $R^{14}$ taken together are $-(CH_2)_3-$ or $-(CH_2)_4-$ thus completing a five- or six-membered ring;

$R^{15}$ and $R^{16}$ are each independently selected from hydrogen, alkyl, substituted alkyl, aryl and aryl-alkylene-;

n is zero or one;

p is zero or an integer from 1 to 6;

q is zero or an integer from 1 to 3;

r is zero or one;

the term "alkyl" refers to straight or branched chain radicals of one to seven carbon atoms;

the term "lower alkyl" refers to straight or branched chain radicals of one to four carbon atoms;

the term "substituted alkyl" refers to such straight or branched chain radicals of one to seven carbons wherein one or more hydrogens have been replaced by a hydroxy, amino, cyano, halo, trifluoromethyl, —NH(lower alkyl), —N(lower alkyl)$_2$, lower alkoxy, lower alkylthio, or carboxy;

the terms "lower alkoxy" and "lower alkylthio" refer to such lower alkyl groups as defined above attached to oxygen or sulfur atom, respectively;

the term "cycloalkyl" refers to saturated rings of 3 to 7 carbon atoms;

the term "alkenyl" refers to straight or branched chain radicals of 3 to 7 carbon atoms having one or two double bonds;

the term "substituted alkenyl" refers to such straight or branched chain radicals of 3 to 7 carbon atoms having one or two double bonds wherein a hydrogen has been replaced by hydroxy, amino, halo, trifluoromethyl, cyano, —NH(lower alkyl), —N(lower alkyl)$_2$, lower alkoxy, lower alkylthio, or carboxy;

the term "alkylene" refers to straight or branched chain radicals having one to seven carbon atoms;

the term "aryl" refers to phenyl, 1-naphthyl, and 2-naphthyl;

the term "substituted aryl" refers to phenyl, 1-naphthyl, and 2-naphthyl having a substituent selected from lower alkyl, lower alkoxy, lower alkylthio, halo, hydroxy, trifluoromethyl, amino, —NH(lower alkyl), —N(lower alkyl)$_2$, and di and tri-substituted phenyl, 1-naphthyl, and 2-naphthyl wherein said substituents are selected from methyl, methoxy, methylthio, halo, hydroxy, and amino;

the term "heteroaryl" refers to 2-pyridyl, 3-pyridyl, 4-pryridyl, 4-imidazolyl, 4-thiazolyl, 2-thienyl, 3-thienyl, 2-furyl, 3-furyl, 2-indolyl, 3-indolyl, 4-quinolinyl, and 5-quinolinyl; and the term "halo" refers to chloro, bromo, fluoro and iodo.

2. A compound of claim 1, wherein A is

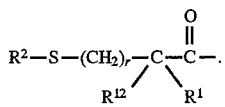

3. A compound of claim 1, wherein A is

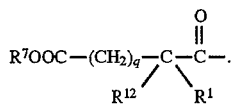

4. A compound of claim 1, wherein A is

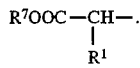

5. A compound of claim 1, wherein A is

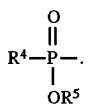

6. A compound of claim 1, wherein A is

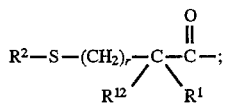

$R^1$, $R^2$ and $R^3$ are each hydrogen;
$R^{12}$ is benzyl;
$R^{13}$ is alkyl;
$R^{14}$ is hydrogen or $R^{13}$ and $R^{14}$ taken together are —(CH$_2$)$_3$— or —(CH$_2$)$_4$— thus completing a five- or six-membered ring;
n is one; and
r is zero.

7. A compound of claim 6, wherein
$R^{13}$ is butyl; and
$R^{14}$ is hydrogen.

8. A compound of claim 6, wherein $R^{13}$ and $R^{14}$ taken together are —(CH$_2$)$_3$— thus completing a five-membered ring.

9. A compound of claim 6, wherein $R^{13}$ and $R^{14}$ taken together are —(CH$_2$)$_4$— thus completing a six-membered ring.

10. A compound of claim 1, selected from the group consisting of:
[3S-[3α(R*),5aα]]-decahydro-3-[(2-mercapto-1-oxo-3-phenylpropyl)amino]-2-oxopyrido[1,2-b][1,2]diazepine-1-acetic acid;
[3S-[3α(R*),5aα]]-octahydro-3-[(2-mercapto-1-oxo-3-phenylpropyl)amino]-2-oxo-1H-pyrrolo[1,2-b][1,2]-diazepine-1-acetic acid; and
[3S-[3α6β(R*)]]-3-butylhexahydro-6-[(2-mercapto-1-oxo-3-phenylpropyl)amino]-7-oxo-1H-1,2-diazepine-1-acetic acid.

11. A pharmaceutical composition useful in the treatment of cardiovascular diseases comprising a pharmaceutically acceptable carrier and at least one compound of the formula

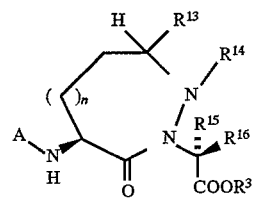

and pharmaceutically acceptable salts thereof wherein:

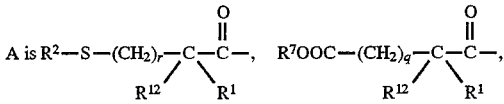

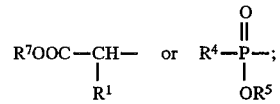

$R^1$ and $R^{12}$ are each independently selected from hydrogen, alkyl, alkenyl, cycloalkyl, substituted alkyl, substituted alkenyl, aryl, substituted aryl, heteroaryl, cycloalkyl-alkylene-, aryl-alkylene-, substituted aryl-alkylene- and heteroaryl-alkylene-, or $R^1$ and $R^{12}$ taken together with the carbon atom to which they are attached complete a cycloalkyl ring or a benzofused cycloalkyl ring;

$R^2$ is hydrogen,

or $R^{11}$—S—;

$R^3$, $R^5$ and $R^7$ are each independently selected from hydrogen, alkyl, substituted alkyl, aryl-(CH$_2$)$_p$—, substituted aryl-(CH$_2$)$_p$—, heteroaryl-(CH$_2$)$_p$—,

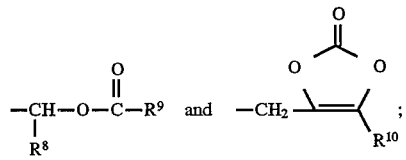

$R^4$ is alkyl, cycloalkyl-(CH$_2$)$_p$—, substituted alkyl, aryl-(CH$_2$)$_p$—, substituted aryl-(CH$_2$)$_p$— or heteroaryl-(CH$_2$)$_p$—;

$R^6$ is alkyl, substituted alkyl, cycloalkyl-(CH$_2$)$_p$—, aryl-(CH$_2$)$_p$—, substituted aryl-(CH$_2$)$_p$— or heteroaryl-(CH$_2$)$_p$—;

$R^8$ is hydrogen, lower alkyl, cycloalkyl or phenyl;

$R^9$ is hydrogen, lower alkyl, lower alkoxy or phenyl;

$R^{10}$ is lower alkyl or aryl-(CH$_2$)$_p$—;

$R^{11}$ is hydrogen, alkyl, substituted alkyl, cycloalkyl-(CH$_2$)$_p$—, aryl-(CH$_2$)$_p$—, substituted aryl-(CH$_2$)$_p$— or heteroaryl-(CH$_2$)$_p$—, or —S—$R^{11}$ completes a symmetrical disulfide wherein $R^{11}$is

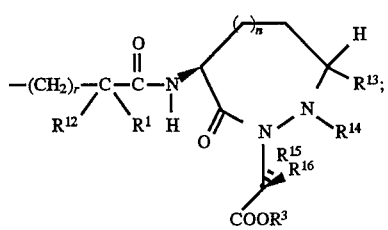

$R^{13}$ is alkyl, aryl, or aryl-alkylene-;

$R^{14}$ is hydrogen, alkyl, aryl or aryl-alkylene, or $R^{13}$ and $R^{14}$ taken together are —$(CH_2)_3$— or —$(CH_2)_4$— thus completing a five- or six-membered ring;

$R^{15}$ and $R^{16}$ are each independently selected from hydrogen, alkyl, substituted alkyl, aryl and aryl-alkylene;

n is zero or one;

p is zero or an integer from 1 to 6;

q is zero or an integer from 1 to 3;

r is zero or one;

the term "alkyl" refers to straight or branched chain radicals of one to seven carbon atoms;

the term "lower alkyl" refers to straight or branched chain radicals of one to four carbon atoms;

the term "substituted alkyl" refers to such straight or branched chain radicals of one to seven carbons wherein one or more hydrogens have been replaced by a hydroxy, amino, cyano, halo, trifluoromethyl, —NH(lower alkyl), —N(lower alkyl)$_2$, lower alkoxy, lower alkylthio, or carboxy;

the terms "lower alkoxy" and "lower alkylthio" refer to such lower alkyl groups as defined above attached to oxygen or sulfur atom, respectively;

the term "cycloalkyl" refers to saturated rings of 3 to 7 carbon atoms;

the term "alkenyl" refers to straight or branched chain radicals of 3 to 7 carbon atoms having one or two double bonds;

the term "substituted alkenyl" refers to such straight or branched chain radicals of 3 to 7 carbon atoms having one or two double bonds wherein a hydrogen has been replaced by hydroxy, amino, halo, trifluoromethyl, cyano, —NH(lower alkyl), —N(lower alkyl)$_2$, lower alkoxy, lower alkylthio, or carboxy;

the term "alkylene" refers to straight or branched chain radicals having one to seven carbon atoms;

the term "aryl" refers to phenyl, 1-naphthyl, and 2-naphthyl;

the term "substituted aryl" refers to phenyl, 1-naphthyl, and 2-naphthyl having a substituent selected from lower alkyl, lower alkoxy, lower alkylthio, halo, hydroxy, trifluoromethyl, amino, —NH(lower alkyl), —N(lower alkyl)$_2$, and di and tri-substituted phenyl, 1-naphthyl, and 2-naphthyl wherein said substituents are selected from methyl, methoxy, methylthio, halo, hydroxy, and amino;

the term "heteroaryl" refers to 2-pyridyl, 3-pyridyl, 4-pyridyl, 4-imidazolyl, 4-thiazolyl, 2-thienyl, 3-thienyl, 2-furyl, 3-furyl, 2-indolyl, 3-indolyl, 4-quinolinyl, and 5-quinolinyl; and the term "halo" refers to chloro, bromo, fluoro and iodo.

12. A method of treating cardiovascular diseases in a mammal which comprises administering to said mammal an effective amount of the composition of claim 11.

13. A compound of the formula

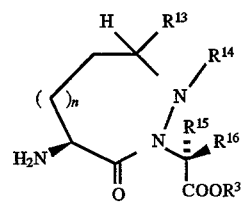

wherein:

$R^{13}$ is alkyl, aryl, or aryl-alkylene-;

$R^{14}$ is hydrogen, alkyl, aryl or aryl-alkylene- or $R^{13}$ and $R^{14}$ taken together are —$(CH_2)_3$— or —$(CH_2)_4$— thus completing a five- or six-membered ring;

$R^{15}$ and $R^{16}$ are each independently selected from hydrogen, alkyl, substituted alkyl, aryl and aryl-alkylene-;

$R^3$ is hydrogen, alkyl, substituted alkyl, aryl-$(CH_2)_p$—, or substituted aryl-$(CH_2)_p$—;

n is zero or one;

p is zero or an integer from 1 to 6;

the term "alkyl" refers to straight or branched chain radicals of one to seven carbon atoms;

the term "lower alkyl" refers to straight or branched chain radicals of one to four carbon atoms;

the term "substituted alkyl" refers to such straight or branched chain radicals of one to seven carbons wherein one or more hydrogens have been replaced by a hydroxy, amino, cyano, halo, trifluoromethyl, —NH(lower alkyl), —N(lower alkyl)$_2$, lower alkoxy, lower alkylthio, or carboxy;

the terms "lower alkoxy" and "lower alkylthio" refer to such lower alkyl groups as defined above attached to oxygen or sulfur atom, respectively;

the term "alkylene" refers to straight or branched chain radicals having one to seven carbon atoms;

the term "aryl" refers to phenyl, 1-naphthyl, and 2-naphthyl;

the term "substituted aryl" refers to phenyl, 1-naphthyl, and 2-naphthyl having a substituent selected from lower alkyl, lower alkoxy, lower alkylthio, halo, hydroxy, trifluoromethyl, amino, —NH(lower alkyl), —N(lower alkyl)$_2$, and di and tri-substituted phenyl, 1-naphthyl, and 2-naphthyl wherein said substituents are selected from methyl, methoxy, methylthio, halo hydroxy, and amino; and the term "halo" refers to chloro, bromo, fluoro and iodo.

14. A compound of claim 13 wherein:

$R^{13}$ is alkyl;

$R^{14}$ is hydrogen or $R^{13}$ and $R^{14}$ taken together are —$(CH_2)_3$— or —$(CH_2)_4$— thus completing a five- or six-membered ring.

15. The compound of claim 14 wherein:

$R^{13}$ is butyl;

$R^{14}$ is hydrogen;

$R^{15}$ and $R^{16}$ are both hydrogen;

n is one; and $R^3$ is ethyl.

16. The compound of claim 14 wherein:

$R^{13}$ and $R^{14}$ taken together are —$(CH_2)_3$— thus completing a five-membered ring;

$R^{15}$ and $R^{16}$ are both hydrogen;

n is one; and $R^3$ is ethyl.

17. The compound of claim 14 wherein:

$R^{13}$ and $R^{14}$ taken together are —$(CH_2)_4$— thus completing a six-membered ring;

$R^{15}$ and $R^{16}$ are both hydrogen;

n is one; and $R^3$ is ethyl.

* * * * *